(12) United States Patent
Epstein

(10) Patent No.: US 10,793,891 B2
(45) Date of Patent: Oct. 6, 2020

(54) NANOFLUIDIC DEVICE FOR ISOLATING, GROWING, AND CHARACTERIZING MICROBIAL CELLS

(71) Applicant: Northeastern University, Boston, MA (US)

(72) Inventor: Slava Epstein, Dedham, MA (US)

(73) Assignee: Northeastern University, Boston, MA (US)

(*) Notice: Subject to any disclaimer, the term of this patent is extended or adjusted under 35 U.S.C. 154(b) by 237 days.

(21) Appl. No.: 15/683,136

(22) Filed: Aug. 22, 2017

(65) Prior Publication Data

US 2018/0037924 A1    Feb. 8, 2018

Related U.S. Application Data

(63) Continuation of application No. 14/388,901, filed as application No. PCT/US2013/033968 on Mar. 27, 2013, now Pat. No. 10,626,435.

(60) Provisional application No. 61/616,501, filed on Mar. 28, 2012, provisional application No. 61/616,467, filed on Mar. 28, 2012.

(51) Int. Cl.

| B01L 3/00 | (2006.01) |
| C12M 1/00 | (2006.01) |
| C12M 1/34 | (2006.01) |
| C12M 3/06 | (2006.01) |
| C12Q 1/02 | (2006.01) |
| C12Q 1/18 | (2006.01) |
| G01N 33/543 | (2006.01) |
| G01N 33/58 | (2006.01) |

(52) U.S. Cl.
CPC ........ *C12Q 1/025* (2013.01); *B01L 3/502707* (2013.01); *C12M 1/34* (2013.01); *C12M 23/16* (2013.01); *C12M 23/34* (2013.01); *C12Q 1/18* (2013.01); *G01N 33/54373* (2013.01); *G01N 33/585* (2013.01); *B01L 2200/0668* (2013.01); *B01L 2300/0816* (2013.01); *B01L 2300/0861* (2013.01); *B01L 2300/0896* (2013.01); *B01L 2400/0472* (2013.01); *Y10T 156/10* (2015.01)

(58) Field of Classification Search
CPC ....... B01L 3/502707; B01L 2200/0668; B01L 2300/0816; B01L 2300/0861; B01L 2300/0896; B01L 2400/0472; G01N 33/585; G01N 33/54373; C12M 1/34; C12M 23/16; C12M 23/34; C12Q 1/18; C12Q 1/025; Y10T 156/10
USPC .................................................... 435/305.2
See application file for complete search history.

(56) References Cited

U.S. PATENT DOCUMENTS

| 6,440,734 B1 | 8/2002 | Pykett et al. |
| 7,767,435 B2 | 8/2010 | Chiu et al. |

(Continued)

OTHER PUBLICATIONS

Severine Le Gac et al. "Single cells as experimentation units in lab-on-a-chip devices; 55-62". (Year: 2009).*

(Continued)

*Primary Examiner* — Liban M Hassan
(74) *Attorney, Agent, or Firm* — Verrill Dana, LLP

(57) ABSTRACT

Nanofluidic devices and methods of the invention are capable of autonomously isolating individual microbial cells using constrictive channels and growing monocultures of the cells for automated characterization of their biochemical properties and interactions with mammalian cells. Single microbial cells, such as bacterial cells, are isolated directly from environmental sources and cultured using chemical factors from their native environment.

17 Claims, 13 Drawing Sheets

(56) References Cited

U.S. PATENT DOCUMENTS

| | | |
|---|---|---|
| 2002/0172621 A1 | 11/2002 | Barbera-Guillem |
| 2005/0164376 A1 | 7/2005 | Balagadde |
| 2007/0155016 A1 | 7/2007 | Lee et al. |
| 2008/0017306 A1 | 1/2008 | Liu et al. |
| 2008/0016325 A1 | 3/2008 | Deutsch |
| 2008/0057561 A1 | 3/2008 | Takahashi et al. |
| 2008/0257735 A1 | 10/2008 | Jeon et al. |
| 2010/0041128 A1 | 2/2010 | Banes et al. |
| 2010/0136551 A1 | 6/2010 | Cho et al. |
| 2010/0159462 A1 | 6/2010 | Takayama et al. |

OTHER PUBLICATIONS

Cookson et al. "Monitoring dynamics of single-cell gene expression over multiple cell cycles," Molecular Systems Biology, vol. 1, No. 2005.0024, 6 pages (2005).

Lewis et al. "Uncultured microorganisms as a source of secondary metabolites," The Journal of Antibiotics, vol. 63, pp. 468-476 (9 pages), (2010).

Ma, Huipeng et al., "Characterization of the interaction between fibroblasts and tumor cells on a microfluidic co-culture device.", Electrophoresis (2010), 31, pp. 1599-1605 DOI: 10.1002/elps/00900776.

Gavrish, Ekaterina et al., "A trap for in situ cultivation of filamentous actinobacteria." J. Microbiol Methods, vol. 72, No. 3, pp. 257-262 (2008).

Le Gac, Séverine et al., "Single cells as experimentation units in lab-on-a-chip devices." Trends in Biotechnology, vol. 28, Issue 2, Feb. 2010, pp. 55-62 DOI: 10.1016/j.tibtech.2009.10.005.

\* cited by examiner

NANOFLUIDIC DEVICE FOR ISOLATING, GROWING, AND CHARACTERIZING MICROBIAL CELLS

CROSS REFERENCE TO RELATED APPLICATIONS

This application is a continuation application of U.S. application Ser. No. 14/388,901, filed Sep. 29, 2014, which is a national phase application of PCT/US2013/033968, filed Mar. 27, 2013, which claims the priority of U.S. Provisional Application No. 61/616,467 filed Mar. 28, 2012 and entitled "Micro/Nanofluidic Device for Trapping and Manipulating Single Bacterial Cells and Their Local Microenvironment" and U.S. Provisional Application No. 61/616,501, filed Mar. 28, 2012 and entitled "Method and Device for Autonomous Separation of Microorganisms and to Grow and Isolate Novel Species with Unknown Growth Requirements". Each of the aforementioned priority applications is hereby incorporated by reference in its entirety.

STATEMENT REGARDING FEDERALLY SPONSORED RESEARCH OR DEVELOPMENT

N/A

BACKGROUND

There has been little study of microbes based on single-cell experiments due to the difficulties of manipulating single microbial cells. Single cell studies are being used increasingly and providing exciting results that cannot be obtained with other techniques. Analysis of data obtained from individual cells is providing new insights about the machinery and mechanisms at work inside cells. For example, video recording of bacterial cells in microchannels has provided information about motility and biofilm growth. However, single-cell experiments are not yet often employed for investigating microbes. A major reason is the small size of these cells. Bacterial cells are usually 10-100 times smaller than mammalian cells, which makes them much harder to observe and manipulate at the single-cell level. Even within the microfluidic community, their small size (1-10 microns) makes handling bacteria challenging, as most devices have channels that are several hundred micrometers in diameter. To handle bacteria reliably, nanoscale structures and nanofluidics are required. Thus, there remains a need to develop new nanofluidic devices to manipulate individual bacterial and other microbial cells.

Similarly, existing methods for cultivation of microbial cells from natural environments are limited. Once the target environment is sampled, an inoculum from the cells contained in the sample is placed on a nutrient medium. Thus cells have to be moved from their natural environment to an artificial environment and manipulated therein prior to their exposure to a growth permissive condition. Such handling and manipulation is likely to damage cells targeted for cultivation. This may contribute to the well-known phenomenon that only a tiny proportion of cells in a sample will form growth upon inoculation. Thus, there is a need to develop a sampling device that introduces a minimum of handling and would thus be expected to allow growth of the "missing" species of microbes. One such sampling device is the "trap" method of Gavrish, E., A. Bollmann, S. Epstein, and K. Lewis (J Microbiol Methods 72:257-262 (2008)). In that method, the growth chamber is separated from the environment by porous membranes. These contain multiple pores, allowing for multiple species to establish colonies inside, leading to mixed cultures. An ideal microbial sampling device would allow monocultures to be grown from single cells.

SUMMARY OF THE INVENTION

The invention provides devices and methods for autonomously isolating monocultures of microbial cells directly from natural and manmade environments. The devices also support the functional characterization of individual microbial cells, such as bacterial cells, and their biochemistry, physiology, genomics, metabolism, and interaction with other cells, such as other microbial cells or mammalian cells.

One aspect of the invention is a device for isolating and culturing single cells of a population of microbial cells. The device includes: a nanofluidic channel fluidically coupled at a first end to a fluid containing a mixture of microbial cells and a microfluidic food chamber fluidically coupled to a second end of the nanofluidic channel. The nanofluidic channel has a cross-sectional diameter that allows entry of only a single microbial cell from the microfluidic channel and prevents the microbial cell from entering the food chamber; however, the nanofluidic channel allows the progeny of the single microbial cell, but no other cells, to enter the food chamber. In one embodiment, the device also includes a microfluidic channel for introducing a fluid containing the mixture of microbial cells into the device through an inlet port connected to the microfluidic channel. The microfluidic channel is fluidically coupled to the first end of the nanofluidic channel. In an alternative embodiment, the first end of the nanofluidic channel opens on a surface of the device which is in contact with the external environment. In this alternative embodiment, a mixture of microbial cells from the external environment is sampled; chemoattractant factors diffusing from the food chamber and through the nanofluidic channel can induce a microbial cell to enter the first end of the nanofluidic channel from the external environment. In certain embodiments, the food chamber is accessible through a port or opening on its upper surface, to allow for filling with culture medium and harvesting of cultured cells growing in the food chamber.

The nanofluidic channel has a cross-sectional diameter that is large enough to permit the entry of a single microbial cell of interest, such as a bacterial cell, yet small enough to prevent the cell from passing completely through the channel, causing the cell to become lodged in the channel, blocking the subsequent entry of other microbial cells. In certain embodiments, the device contains a transparent window on at least one side of the food chamber, or is fully transparent, allowing for light microscopic observation of microbial cells in the food chamber, or throughout the device. In some embodiments, the microbial cells contain a fluorescent label and can be tracked using fluorescence microscopy. The microfluidic channel, on the other hand, if present, has a cross-sectional diameter large enough (e.g., from about 10 µm to about 1000 µm) to permit two or more cells to travel down the channel. The food chamber contains a culture medium in which the microbial cells of interest can survive and reproduce. When a cell becomes lodged in the nanofluidic channel, its progeny can grow toward the food chamber and eventually reach the food chamber and grow there to form a monoculture derived from the single microbial cell that became lodged in the nanofluidic channel.

In some embodiments, the device contains a plurality of microfluidic food chambers, each of which is fluidically coupled to the microfluidic channel by a separate nanofluidic channel. For example, a single device can include 10 or more, or 100 or more, or even 1000 or more food chambers, each linked to a single nanofluidic channel that communicates with one or more common microfluidic channels that supply a mixture of microbial cells to be separated. In this way, a plurality of monocultures can be obtained simultaneously, each derived from a different individual cell present in the mixture fed into the microfluidic channel. In some embodiments, the various food chambers contain different culture media, so that the requirements of different microbial species can be met.

Certain embodiments of the device contain a membrane at one face of the food chamber. The membrane permits entry of nutrients from an environment outside the food chamber but retains microbial cells within the food chamber. This embodiment can make possible the culture of microbial cells that will only survive and grow in the presence of chemical factors and/or nutrients which are unknown but which are present in the natural environment where the organism is normally found.

In yet other embodiments of the device, a face of the food chamber contains a sensor surface that can be used to study and characterize microbial cells that are present in the chamber. For example, the sensor surface can include gold or silver nanoparticles, and can be suitable for performing surface plasmon resonance imaging, surface-enhanced Raman spectroscopy, or electrochemical measurements to characterize microbial cells in the food chamber.

Another embodiment of the device is one that is integrated into a circuit, such as part of an integrated circuit or CMOS device.

Still another aspect of the invention is a method of fabricating the device described above. The method includes the steps of: (a) providing a template comprising a first substrate, a nanoscale strip deposited on the first substrate, and a first microscale structure deposited on the first substrate and attached to a first end of the nanoscale strip; (b) polymerizing an elastic polymer material on the template; (c) removing the elastic polymer material from the template; and (d) attaching the elastic polymer material to a second substrate, whereby the second substrate seals open spaces in the elastic polymer material formed by the nanoscale strip and the first microscale structure; and whereby the first microscale structure forms the microscale food chamber of the device, and the nanoscale strip forms the nanofluidic channel of the device.

Yet another aspect of the invention is a method of isolating and culturing a single microbial cell to obtain a monoculture of microbial cells. The method includes the steps of: (a) depositing a fluid sample containing a mixture of microbial cells into the inlet port of the device described above, wherein the food chamber of the device contains a culture medium containing a chemoattractant for at least one microbial cell in the sample and capable of supporting the growth and reproduction of said microbial cell; (b) allowing said microbial cell to migrate into the nanofluidic channel of the device; (c) maintaining the device under conditions suitable for allowing said microbial cell to divide within the nanofluidic channel and produce progeny, whereby the progeny eventually enter the food chamber; (d) maintaining the device under conditions suitable for the progeny entering the food chamber to multiply in the food chamber, forming a monoculture of microbial cells.

Another aspect of the invention is a device for characterizing a microbial cell response. The device includes: a first microfluidic channel comprising a sensor surface, and a pair of valves in the first microfluidic channel. The valves of the pair are disposed on opposite sides of the sensor surface and are capable of trapping individual microbial cells flowing through the first microfluidic channel on the sensor surface. Responses of a microbial cell trapped on the sensor surface can be characterized by a method such as surface plasmon resonance imaging, surface enhanced Raman spectroscopy, or electrochemical analysis.

BRIEF DESCRIPTION OF THE DRAWINGS

FIG. 3A is a micrograph using a red filter, showing that the mCherry expressing bacteria have migrated into the constriction channel, and a single mCherry expressing bacterium has entered the food channel. FIG. 3B shows the same view through a green filter; none of the GFP bacteria have entered either the constriction or the food channel. FIG. 3C shows a superposition of the images in 3A and 3B.

DETAILED DESCRIPTION OF THE INVENTION

Figure 1A:
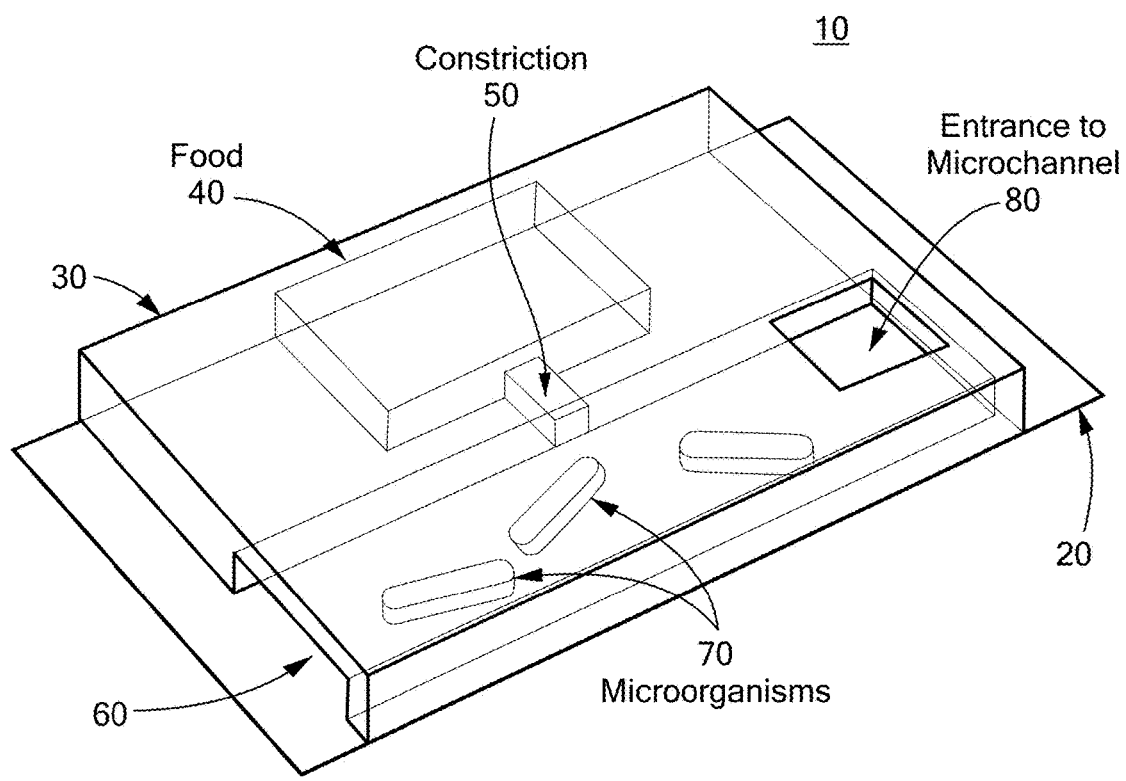
FIG. 1A is a drawing of an embodiment of a nanofluidic device of the invention, in which microbial cells in a microfluidic channel (microchannel) are attracted to enter a nanofluidic channel (constriction) connected to food chamber, where a monoculture of microbial cells can grow.

Devices and methods of the invention combine the use of microfluidics and nanofluidics to manipulate single cells of microbes such as bacteria, algae, fungi, or protozoa, so that they can be either studied at the single cell level or cultured in controlled environments. The devices and methods of the invention are not intended for the isolation of cells derived from more developed species, such a mammals, or of viruses, although such cells or viruses may be studied together with microbial cells in the devices of the invention.

Nanofluidics devices of the invention include one or more nanofluidic channels (also referred to as nanochannels) or constrictions having cross-sectional dimension (e.g., diameter) in the nanometer range, such as from about 250 nm to about 1000 nm, or about 500 nm, 600 nm, 700 nm, 800 nm, or 900 nm, and extending in length for about 1 µm to about 50 µm or more. The nanochannels are fluidically coupled with one or more microfluidic channels (also referred to as microchannels) also present in the device, or with an environmental space present at a surface of the device. Two channels or spaces are "fluidically coupled" if a fluid in one can move freely into the other through a junction between the two, the junction allowing fluid transfer without significant leakage into other uncoupled spaces.

A key feature of the nanofluidics devices is that they also contain one or more food chambers (also referred to as "food channels" or "isolation chambers"), each of which is fluidically coupled with one or more nanochannels. Each food chamber has a channel or opening that allows it to be supplied with a culture or growth medium for the microorganisms whose isolation is desired. The medium diffuses out through the attached nanochannel, where it can attract the microorganisms by chemotaxis, for example. The width and length of the nanochannel are selected to serve as a constriction, allowing only one or a few single microbial cells to enter the nanochannel and/or to pass through the nanochannel. In a preferred embodiment, the nanochannel is narrow enough so that a single microbial cell can enter the nanochannel, but becomes lodged in the channel and cannot move through the channel. In that way, the cell blocks the channel from passage by other cells. Nevertheless, the cell lodged in the nanochannel is fed through the food chamber and can still divide within the nanochannel. The progeny of the lodged cell will then, usually within several hours to a day or more, make their way into the food chamber where they will establish a monoculture (i.e., an essentially pure culture containing only microbial cells of a single species, variety, or type descended from the originally lodged microbial cell but no other cells. The monoculture can then be studied within the device, or removed from the device for culturing using standard microbiological techniques. The dimensions, volume, and geometry of the food chamber can be any desired size, amount, or shape as required by the user. However, the volume of the food chamber is preferably sufficient to be handled and transferred by commonly available laboratory equipment, such as in the range from about 1 µL to about 100 µL, although it can also be less, such as about 1 nL to about 1 µL, especially in the event the grown or isolated cells are intended for characterization on the device itself.

Referring now to FIG. 1A, nanofluidic device 10 includes substrate 20 (or "second substrate", the "first substrate" being one used in the initial stage of fabrication, see below), body 30, food chamber 40, nanochannel or constriction 50, microchannel 60, and a fluid containing microorganisms 70. An opening or inlet port (80) may also be included for the addition of a fluid containing microorganisms to the microchannel. The substrate can be advantageously constructed of silicon, glass or a polymeric material; it is preferably hydrophilic so as to promote the flow of aqueous media through the fluidic channels and spaces of the device, or if hydrophobic it can be coated or plasma treated to render it hydrophilic. The body of the device can be a polymer material. Preferably it is a somewhat elastic material that can be cast or spun on a master template, polymerized, and then removed by pulling it away from the template. A suitable material is phenyldimethylsiloxane (PDMS). The body of the device is preferably transparent, or at least contains one or more transparent windows, to permit microscopic inspection of the device and monitoring of cells within the device.

Figure 1B:
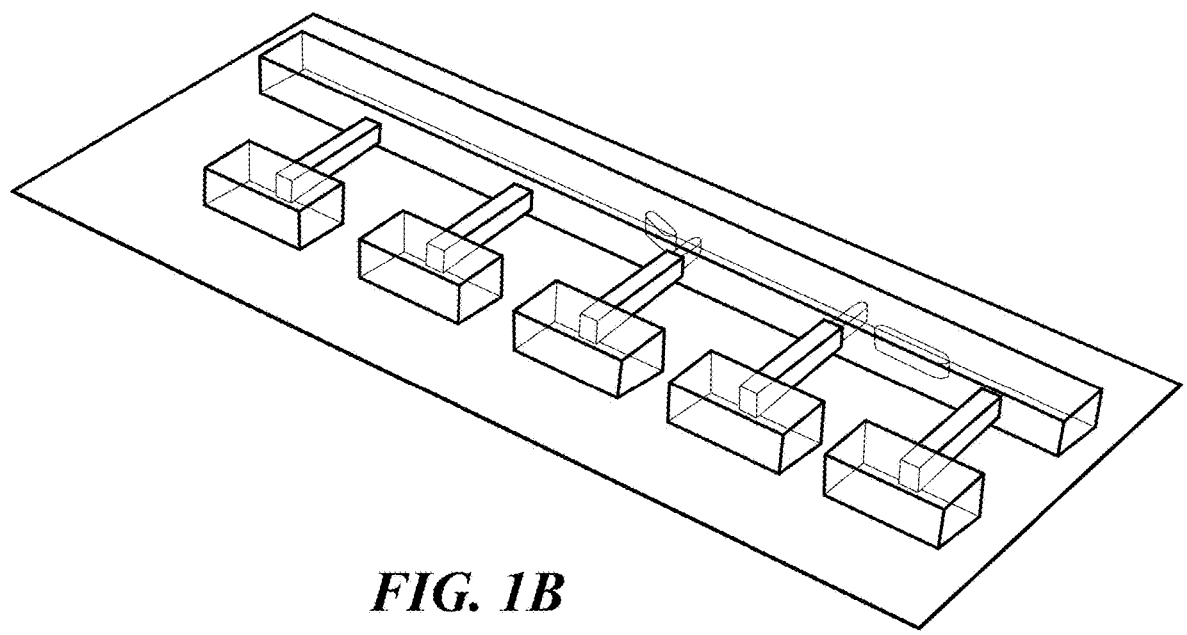
FIG. 1B shows an embodiment of a nanofluidic device of the invention that has multiple food chambers, each linked to a common microfluidic channel by an individual nanofluidic channel. Each food chamber grows a different monoculture derived from an individual microbial cell from the microfluidic channel.

The embodiment shown in FIG. 1B has a plurality (i.e., two or more) of separate food chambers, each fluidically coupled via a unique nanochannel to a common microchannel. A device such as shown in FIG. 1B can be utilized to isolate and culture multiple individual cells from a mixture of different cell types placed into the microchannel. In this manner, a mixture of microbial cells can be autonomously separated and cultured without any input, observation, or manipulation by the user. If desired, the food chambers can contain different types of culture media to suit the growth needs of different cell types, or media containing different chemotactic factors intended to attract certain cell types. Another option is to provide different types of nanochannels, e.g., with different cross-sectional diameters, so as to attract and entrap different types of cells, such as cells of different sizes or ability to deform.

Figure 1C:
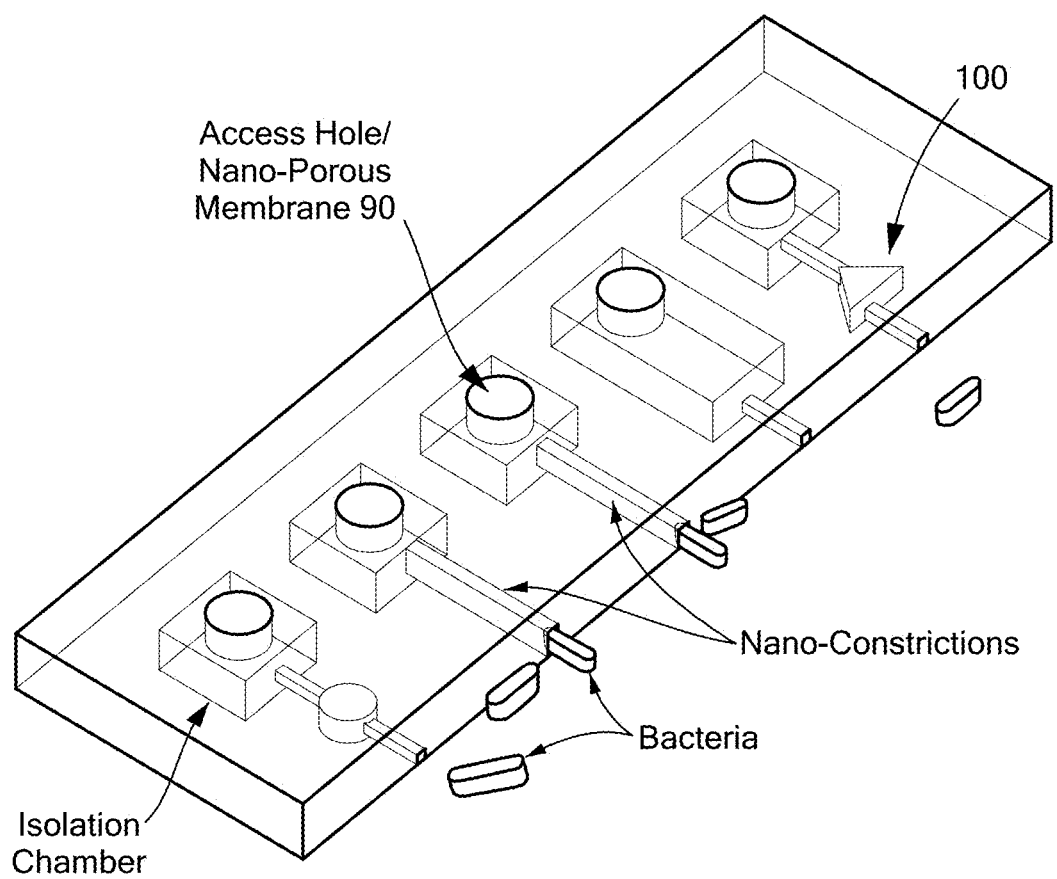
FIG. 1C shows yet another embodiment of a nanofluidic device of the invention. This embodiment includes an enriching chamber disposed between a microfluidic channel and some of the food chambers. It also includes an access hole at the top of each food chamber for recovery of cultured microorganisms. The access hole can also be covered with a membrane that allows chemical factors to enter the food chamber from an environment outside the device.

FIG. 1C shows an embodiment having further optional features. The food chambers are outfitted with access holes 90 for the filling of the chambers with growth media or other substances, and for harvesting of cultured cells after growth has reached a desired stage. The access holes can be closed off by a resealable septum or by a porous membrane. Membranes can be made of polycarbonate or aluminum oxide, or other materials, and preferably have pores of 100 nm or less (e.g., about 30 nm), that allow the diffusion of small molecules, proteins, and nucleic acids through the membrane but retain cells within the food chamber. Such membranes can be used to allow environmental chemical agents to diffuse into the food chamber to assist in the growth or maintenance of cells in the chamber, making it possible to grow and/or maintain cells that are otherwise uncultivable because their growth requirements are unknown, uncharacterized, or different from those supplied by standard microbial culture media. The membranes also can be used to allow chemical agents secreted by the cells in the culture medium (antibiotics or other potentially useful substances) to be recovered for analysis or testing. Yet another use of the membranes is to allow substances to be delivered to cells present in the food chamber to test their effects on the cells, their metabolism, or their growth. A further feature depicted in FIG. 1C is the enriching chamber 100 that can optionally be introduced between the nanochannel that interfaces with the environment (or a microchannel or other reservoir) and the food chamber to assist in preselecting or concentrating certain cells before their admission into the food chamber.

Figure 2:
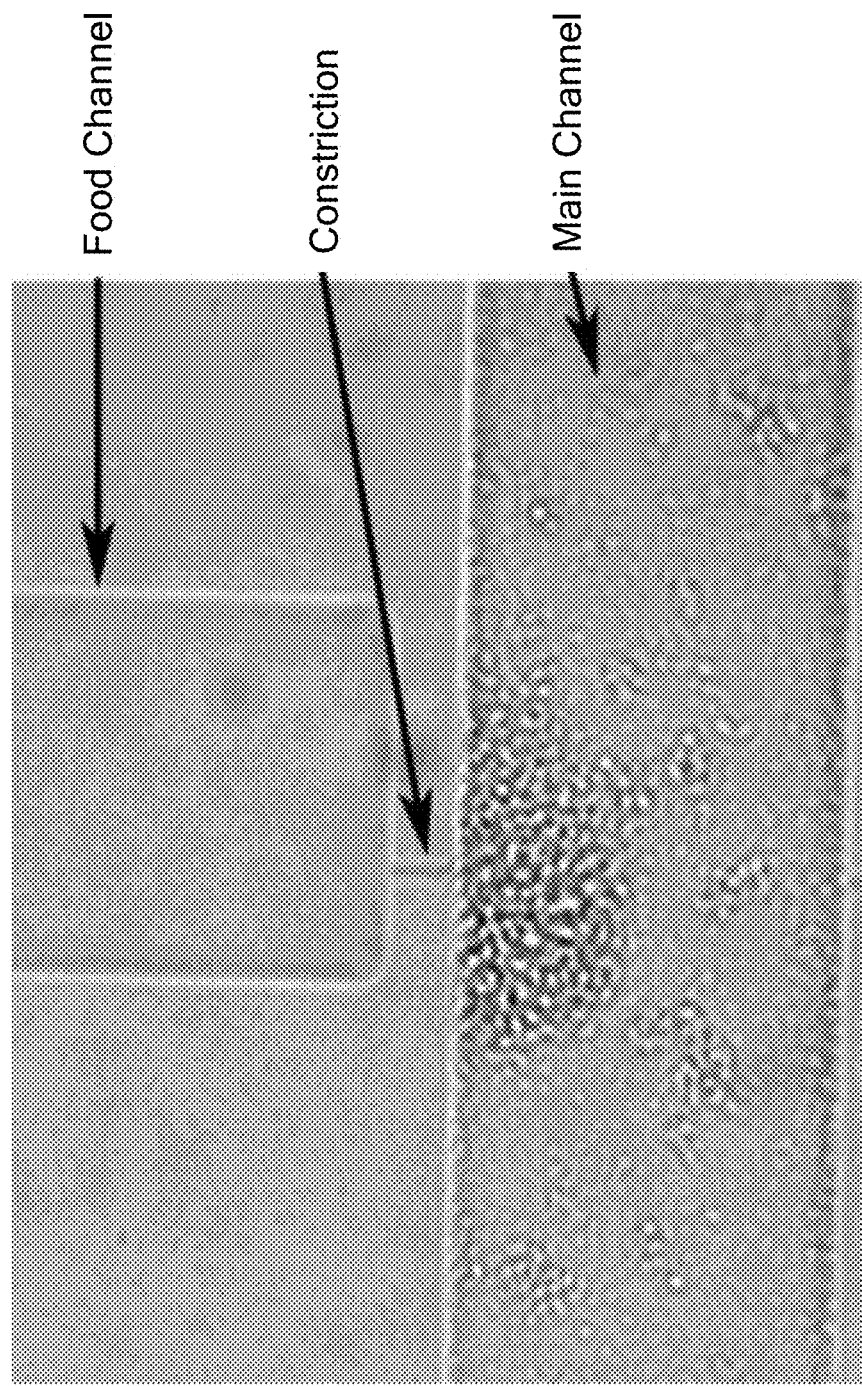
FIG. 2 is a bright field photomicrograph of a nanofluidic device of the invention. A microfluidic channel (main channel) is connected via a nanofluidic channel (constriction) to a food chamber (food channel). The microfluidic channel contains bacteria that have collected into a mass at the entrance to the nanofluidic channel, due to effusion of chemoattractants from the food chamber. The nanofluidic channel is too small to allow the bacteria to pass through into the food channel.

A bright field photomicrograph of a portion of an actual device is shown in FIG. 2. An aqueous solution containing *E. coli* bacteria was introduced into the microchannel show extending horizontally across the bottom. A nanochannel is fluidically coupled to the microchannel at one end and extends vertically upward, where it meets and is fluidically coupled at its other end to a food chamber, which is filled with a bacterial growth medium. The long axis of the nanochannel is oriented perpendicular to the long axis of the microchannel, although other angles would work as well. The nanochannel opens at one end into the food chamber, preferably near the middle of one side of the food chamber, though the exact alignment is not critical. The bacteria are attracted to food slowly leaking out through the nanochannel into the microchannel, and they have gathered in the microchannel at the opening of the nanochannel. This happens quickly, over minutes to a few hours after the bacteria are introduced (long before the food would entirely leak out of the food chamber, which generally would take a day or more). Because the diameter of the nanochannel is too small to allow free travel of the bacteria up into the food chamber, a single bacterium (not visible in this image) becomes lodged at the nanochannel opening, which prevents the remaining bacteria from entering the nanochannel. If a slightly larger diameter nanochannel had been used, or a small-bore microchannel (e.g., diameter about 1 to about 5 µm), then bacteria would have rapidly entered the nanochannel, swum up the channel, and populated the food chamber. However, due to the constriction, the food chamber was still devoid of bacteria at the time when this image was recorded.

Figure 3A:
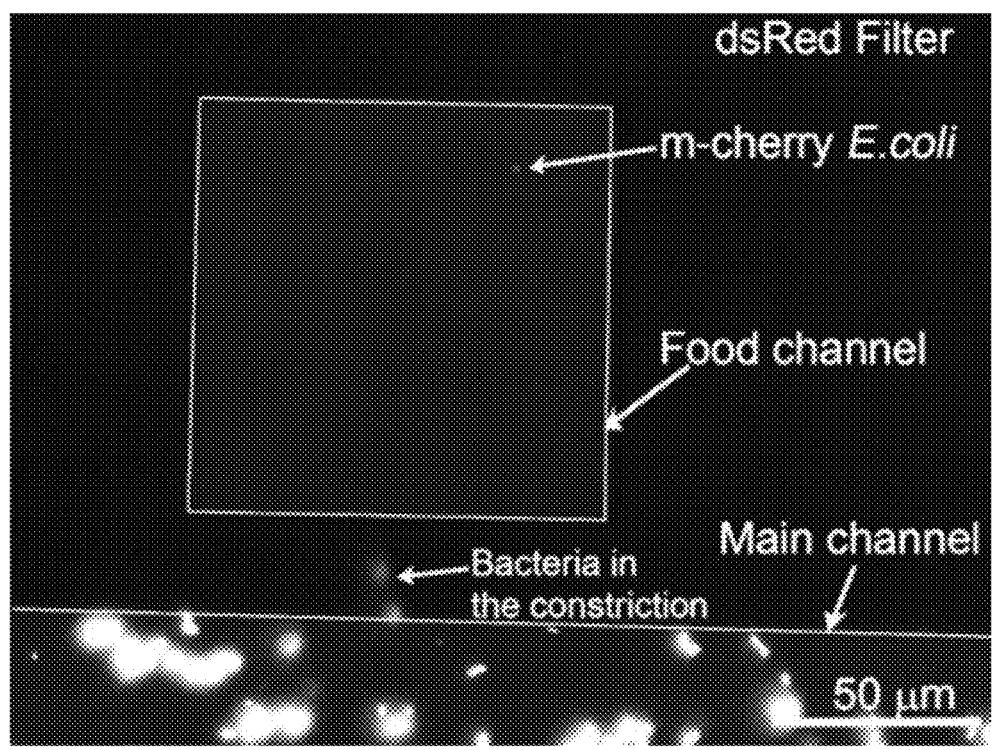
FIGS. 3A-3C show an experiment in which two populations of *Escherichia coli* (*E. coli*) bacteria compete for entry into a food chamber in a nanofluidic device through a constriction (nanofluidic channel). One population of the bacteria expresses green fluorescent protein (GFP) and the other expresses mCherry, a red fluorescent protein.
Figure 3B:
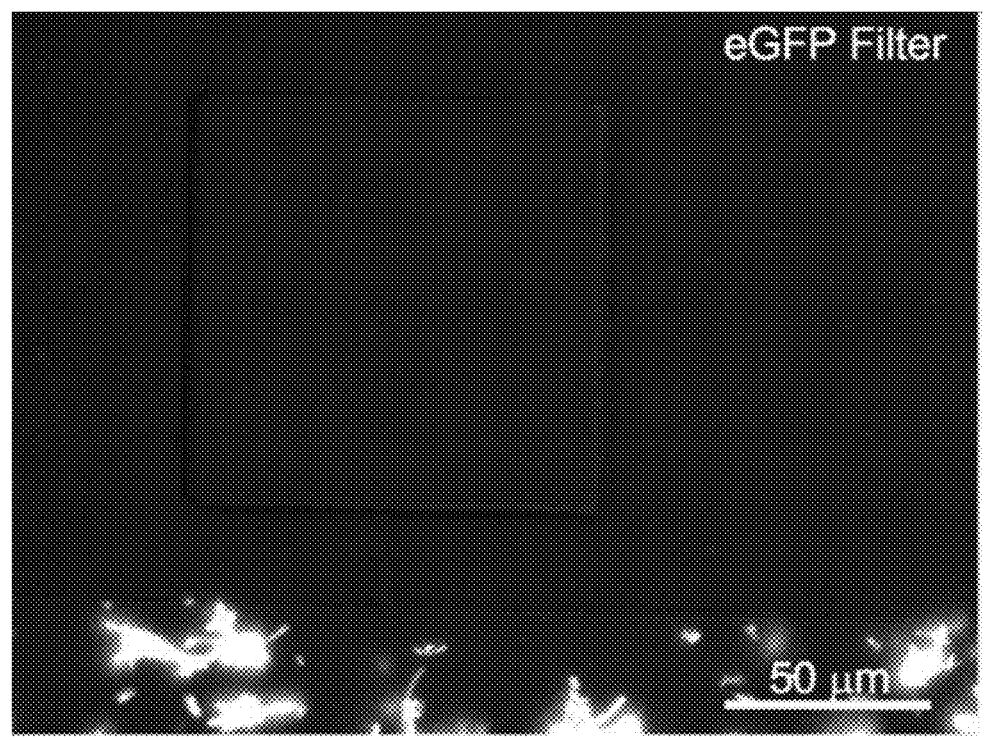
Figure 3C:
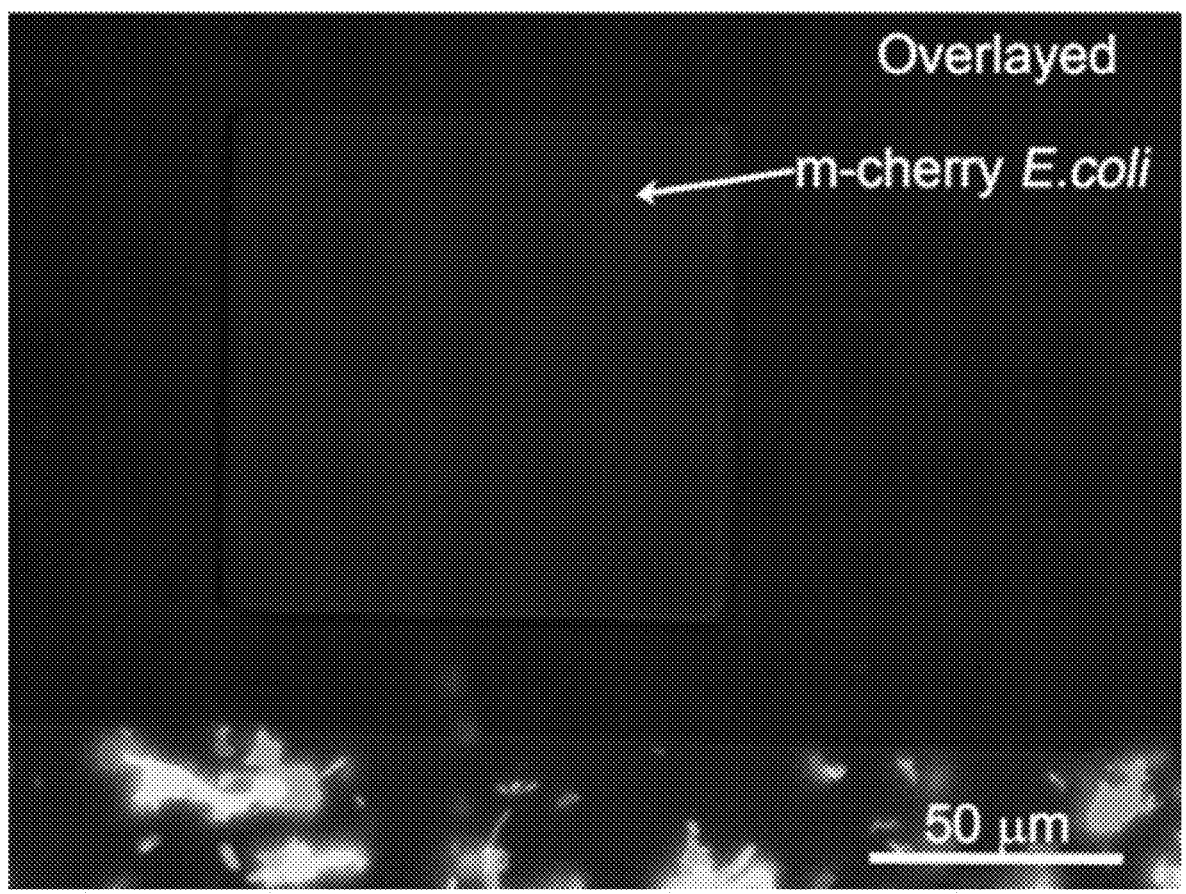

A similar device was used in the experiment depicted in FIGS. 3A-3C. The bacteria in the microchannel were a mixture of two populations of bacteria, one expressing a green fluorescent protein and the expressing a red fluorescent protein. The time course of bacterial migration was monitored using fluorescence microscopy (separate images were recorded using a green filter to show only the GFP and with a red filter to show only the mCherry). At the time this image was recorded, a single mCherry bacterium had entered the food chamber, while the nanofluidic constriction was filled with mCherry expressing bacteria. The microchannel shown at the bottom of the image contained a mixture of red and green fluorescing bacteria, visible as clumps of red and green color as well as their superposition (regions of yellow color), This demonstrates that the device is able to select and isolate a single bacterial cell out of a mixed population of bacteria, and the device accomplishes this autonomously, with no human intervention.

Figure 4:
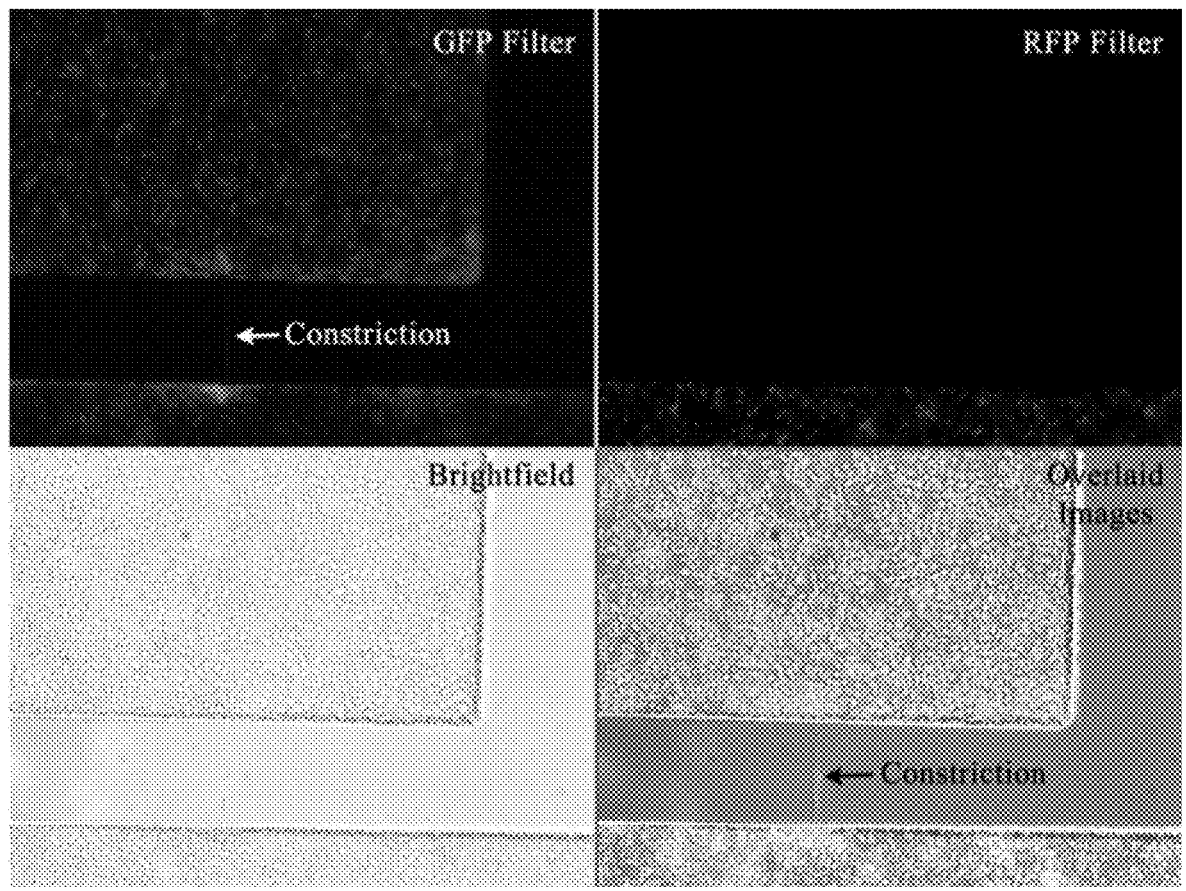
FIG. 4 shows an experiment similar to that in FIGS. 3A-3C, but in this case different species of bacteria are used, *Pseudomonas aeruginosa* (*P. aeruginosa*, labeled with GFP) and *E. coli* (labeled with mCherry, a red fluorescent protein). The upper left panel shows a view of the nanofluidic device through a green filter, the upper right through a red filter, and the lower right shows a composite image of green and red. The lower left image is a brightfield image. It can be seen that the food chamber at the top of the image is filled entirely with *P. aeruginosa* cells (green) and contains no *E. coli* cells (red).

FIG. 4 shows a later result of a similar experiment. In these images it can be seen that the GFP-labeled bacteria, but not the mCherry labeled bacteria, have entered the constriction (see combined brightfield and green fluorescence image at lower right showing green fluorescence in the constriction, compared with the red fluorescence image above, showing no red fluorescence in the constriction) and thoroughly populated the interior space of the food chamber. This demonstrates that a monoculture of bacteria can be obtained in the food chamber after isolation of a single type of bacteria from a mixture, and that the monoculture is obtained well before the food is exhausted or leaks away.

Figure 5:
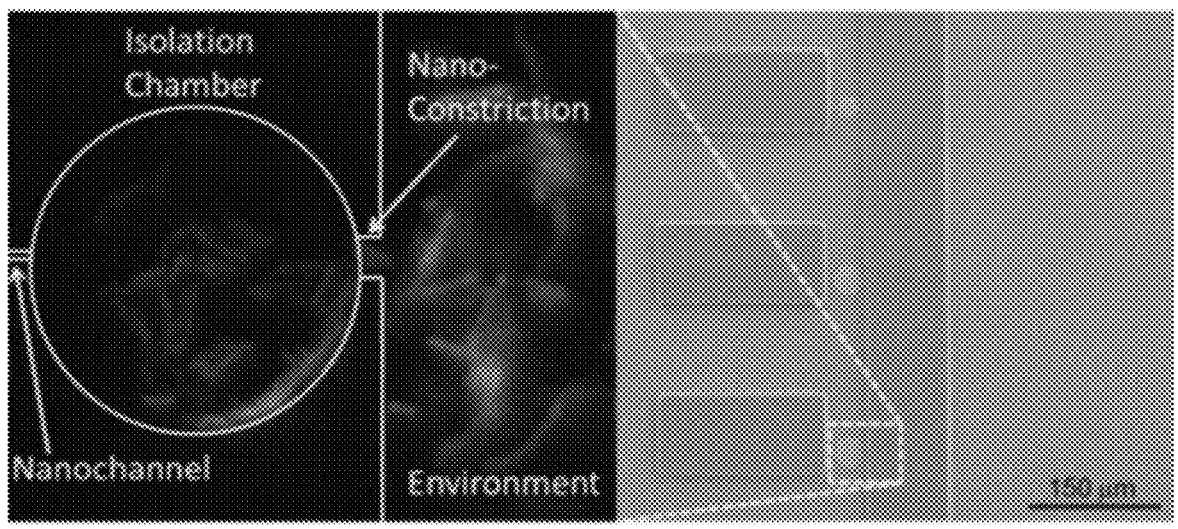
FIG. 5 shows an experiment utilizing an enriching chamber to pre-sort bacterial cells prior to their entry into a food chamber for culture. The right hand panel shows a bright-field micrograph of the nanofluidic device. The indicated lower section is enlarged at left and shown as the superposition of green and red fluorescence. *E. coli* cells expressing GFP and mCherry have migrated into the enriching chamber (isolation chamber), which is populated with almost entirely GFP-expressing cells.

The device shown in FIG. 5 includes an enriching chamber between a microchannel and a food chamber. The enriching chamber in this device has a circular profile, but other shapes could also be used. A constriction of somewhat larger diameter than in the previously described devices (i.e., large enough to prevent a single bacterium from lodging in the channel, but small enough to restrict access to the enrichment chamber) fluidically connects the microchannel and the enrichment chamber, while a smaller nanochannel (small enough to cause a single bacterial cell to lodge in the nanochannel) connects the other end of the enriching chamber to a food chamber (not shown, to the left of the image). Use of GFP- and mCherry-labeled bacteria shows that the enriching chamber contains nearly a monoculture of green bacteria, but still contains a small number of red bacteria. Use of this design increases the likelihood of obtaining a fully pure monoculture in the food chamber. It can also speed up the process of infiltration of the food chamber, as it provides a sheltered and fed environment for a selected mixture of bacteria to congregate.

It is understood that nanofluidic devices of the invention can include any element or feature commonly used in microfluidic or nanofluidic devices, in microelectronic or nanoelectronic devices, or in medical devices. These include, without limitation and in any combination, one or more channels (microscale or nanoscale), reservoirs, ports, holes, valves, air-filled spaces, fluid-filled spaces, waste receptacles, pump mechanisms, vacuum lines or ports, needles, electrical devices or connections, circuitry, sensors, nanoelements (i.e., nanoparticles and/or nanotubes, assembled or free), biomolecules (including peptides, proteins, nucleic acids, sugars, antibodies, lipids, growth factors, cytokines, or metabolites), surface coatings of any kind, membranes, viewing panels, attached tubing or lines, display devices, microprocessors, memory devices, buttons, user interfaces, and wireless transmitters and/or receivers. The devices also can be adapted either for laboratory use, for field use in external natural or manmade environments, including under harsh or extreme conditions, or for implantation into the body or mounting on the surface of a human, animal, or plant, or for harvesting microbes from the air, from surfaces of buildings or inhabited spaces, from a body of water, or from a location submerged in soil, rock, or ice.

Figure 6A:
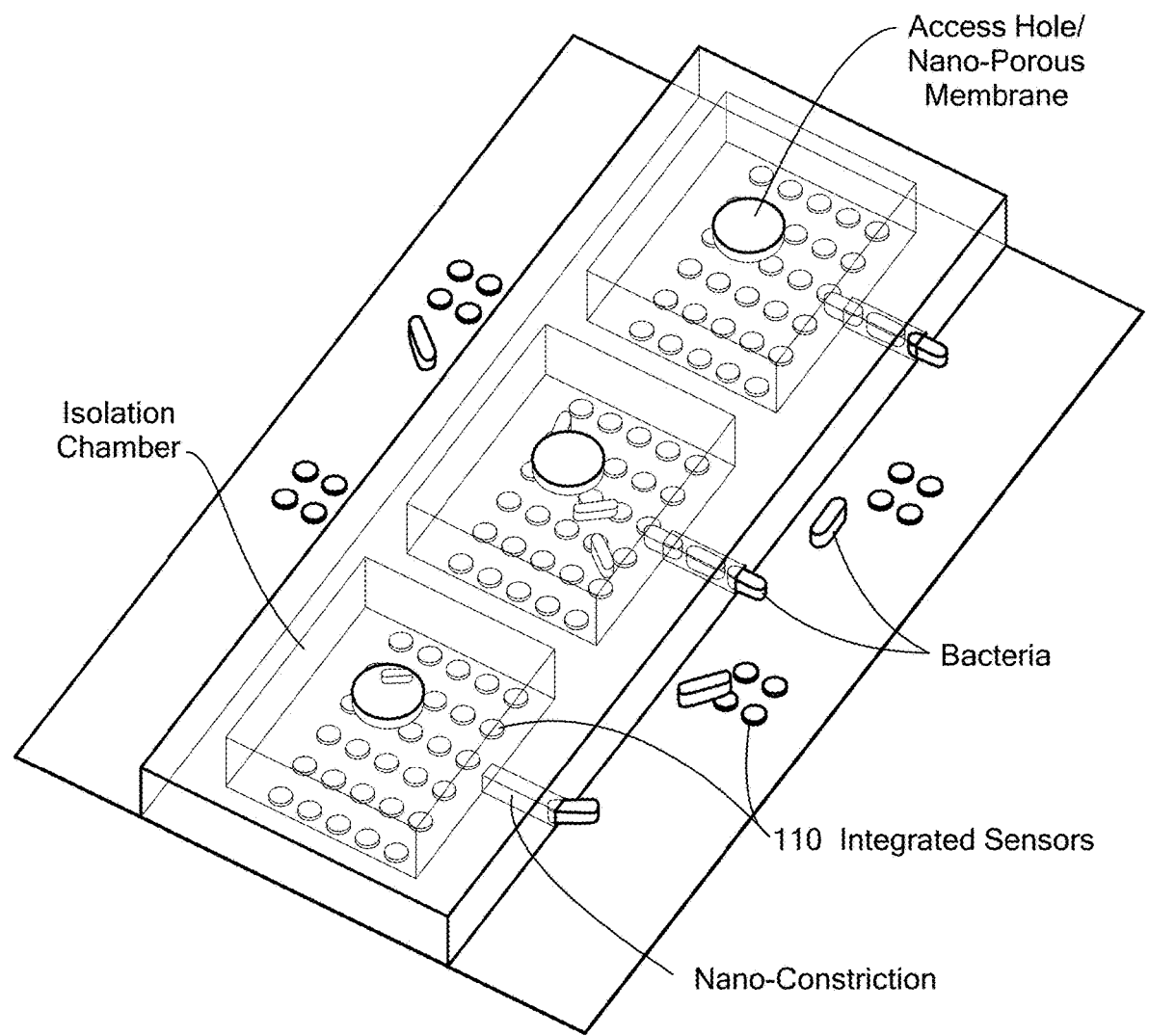
FIG. 6A shows an embodiment of a nanofluidic device of the invention containing integrated sensors embedded in the substrate inside and outside of the food chamber. The sensors in this embodiment are integrated into a microelectronic device.
Figure 6B:
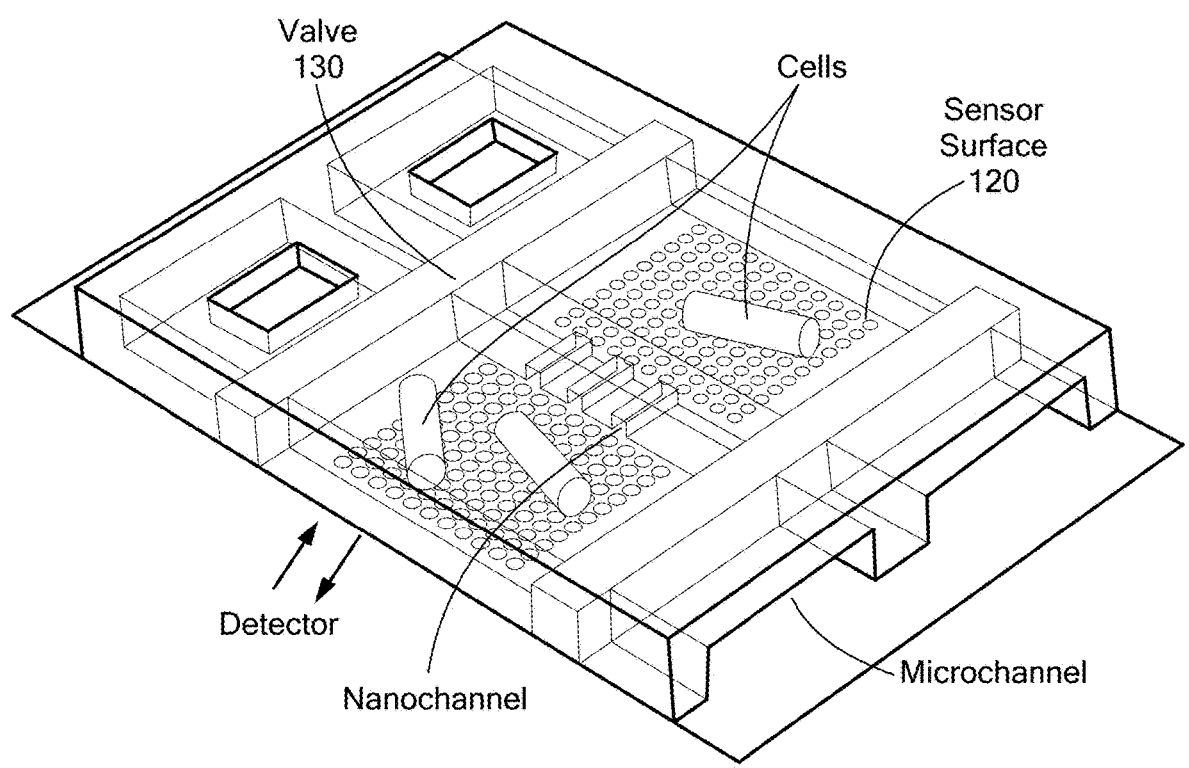
FIG. 6B shows an embodiment having a sensor surface within two microfluidic channels which are connected by nanofluidic channels. Different cells can be isolated in the two sensor chambers through the action of a pair of valves, and their interactions studied during exchange of chemical factors through the nanofluidic channels. In this embodiment, the sensor surface is a nanopatterned gold surface that can be used for studies involving surface plasmon resonance imaging or surface enhanced Raman spectroscopy.
Figure 7A:
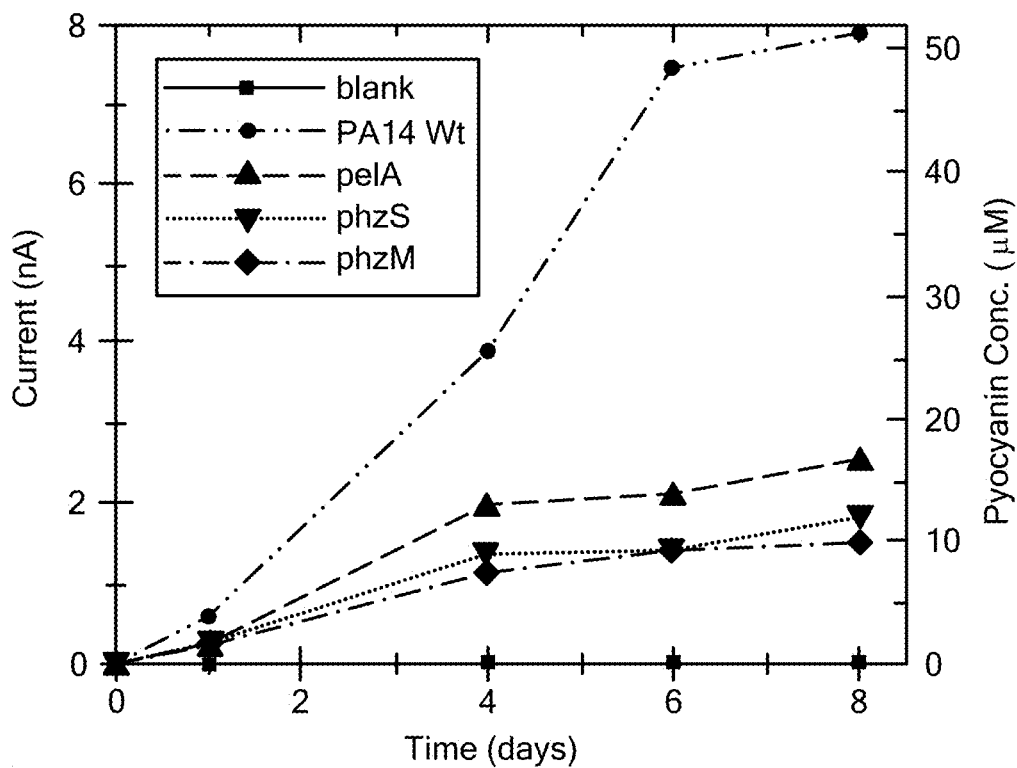
FIGS. 7A and 7B show results obtained using electrochemical sensors in a device similar to that shown in FIG. 6B.
Figure 7B:
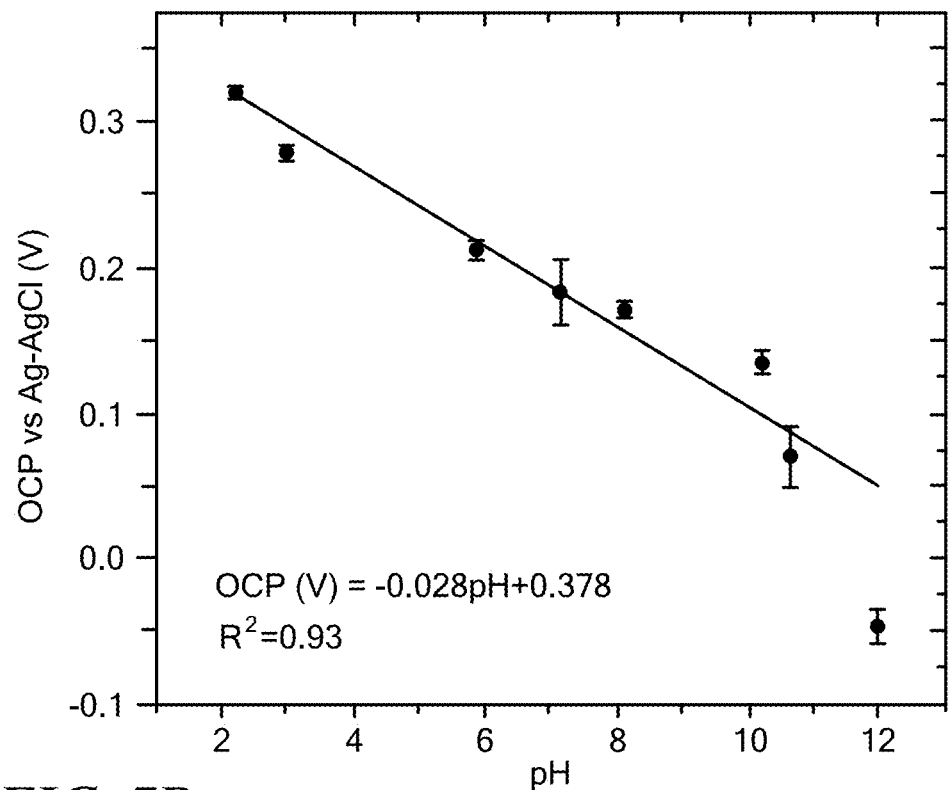

In addition to the type of devices described above, which can be used to autonomously isolate and culture pure cultures of microbial cells from a single progenitor cell from any environment, or from a provided sample containing a mixture of cell types (even including non-microbial cells), nanofluidic devices of the invention also can be constructed for the manipulation and analysis of single microbial cells. In such devices, the food chamber can be either included or it can be omitted as desired. However, the analytical nanofluidic devices are equipped with either one or more sensor elements in a growth or food chamber or an isolation chamber (see, e.g., FIG. 6A, showing sensors 110) or having a sensor surface (see, e.g., FIG. 6B, showing sensor surface 120 and valves 130 for isolating microbial cells for study in an isolation chamber). The sensor surface can include surface coatings to bind microbial cells or special materials, structures, or sensors for analytical techniques. For example, a nanopatterned gold sensor surface (produced by known techniques for patterning a gold surface or produced by depositing gold nanoparticles) can be used in conjunction with non-perturbing optical techniques including imaging with optical or other wavelengths, surface plasmon resonance imaging, or surface enhanced Raman spectroscopy. Sensors such as microelectrodes can be included to perform electrical or electrochemical measurements. FIG. 7 shows data that were obtained using electrochemical sensors. In FIG. 7A shows the accumulation of the toxin pyocyanin secreted over time by the indicated strains of *P. aeruginosa* cells and as detected using microelectrodes and a redox reaction. FIG. 7B demonstrates pH measurement in a nanofluidic device using a microfabricated palladium electrode.

Figure 8:
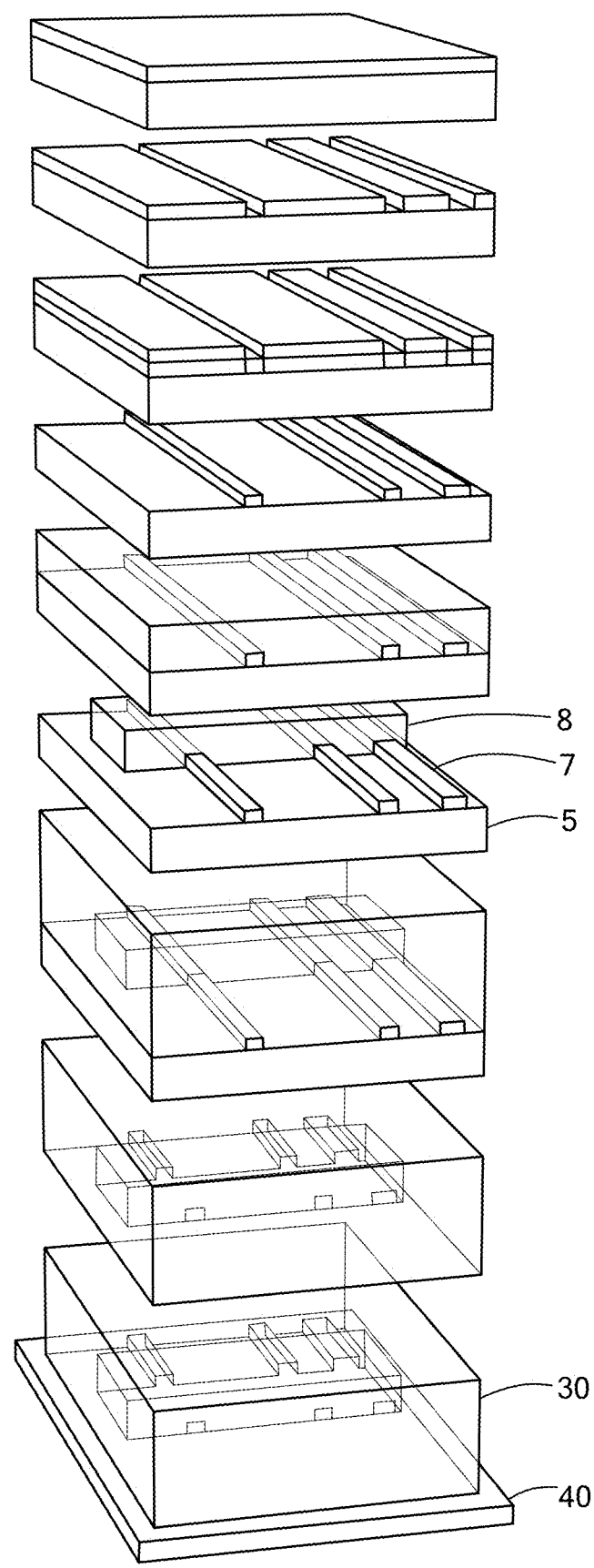
FIG. 8 schematically depicts an embodiment of a fabrication process for making a nanofluidic device of the invention. The steps of the process proceed sequentially from top to bottom, each step resulting in the structure shown.
Figure 9A:
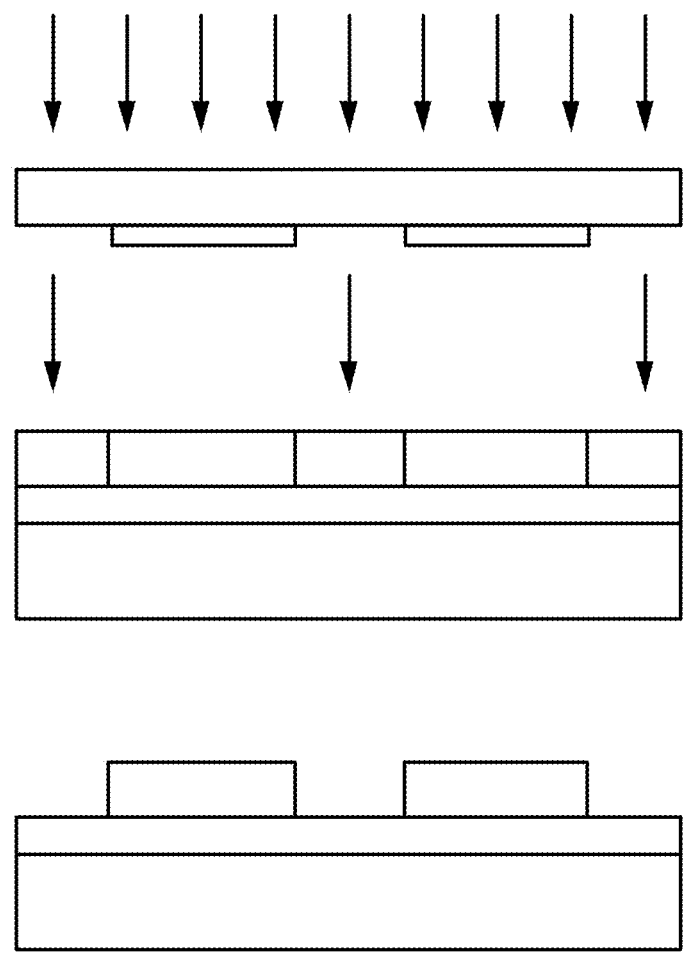
FIGS. 9A-9D schematically depict a process of etching a chromium layer covered by a patterned photoresist to obtain nanoscale strips used to prepare nanofluidic channels or constrictions in a nanofluidic device of the invention.
Figure 9B:
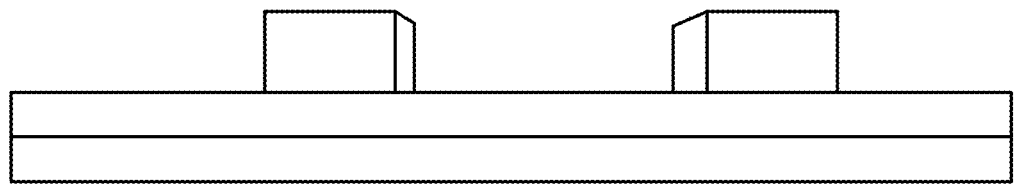
Figure 9C:
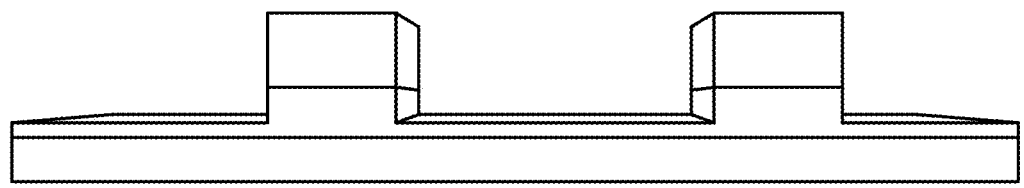
Figure 9D:

The nanofluidic devices described herein can be fabricated using any known technique, including but not limited to micromachining, injection molding, three-dimensional printing, lithography, deposition methods, and any combination thereof. A preferred process is shown in FIG. 8, in which the process is depicted from top to bottom, showing intermediate structures formed after each step. A first substrate (e.g., silicon, silicon dioxide, or a polymer material) is covered with a photoresist (e.g., poly (methylmethacrylate), PMMA), which is patterned using electron beam lithography. The lithography process is used to lay out the form and position of nanostrips that are subsequently produced and used to make the nanofluidic channels of the device. A layer of chromium (or another metal, or a polymeric material) is deposited onto the patterned photoresist, after which removal of the resist leaves chromium nanostrips deposited on the substrate and having the dimensions and layout desired for the nanochannels of the final device. Next, a polymer (e.g., a photoresist such as SU8 or another material) is applied over the substrate and nanostrips (e.g., by spin coating), and the polymer is patterned using, for example, photolithography or electron beam lithography. The pattern creates other hollow, microscale structures of the final device, such as food chambers, microchannels, and the like. This results in a master template that includes nanostrips 7 and microstructures (e.g., microfluidic channels, food chambers, or other microfluidic structures) 8 mounted on first substrate 5. A desired material to be used as body 30 of the device is then applied over the master template and allowed to polymerize or cure. For example, the body can be formed from an elastic polymer material such as phenyldimethylsiloxane (PDMS) and heat cured. Then, the body of the device is mechanically removed (i.e. pulled off) from the template and finally mounted on second substrate 40 to produce the device. The second substrate can be any solid material with desired properties, such as, for example, silicon or glass. The template is preferably reusable for the formation of many devices. The body of the device is sealed to the second substrate so as to prevent fluid leaks. One suitable method of attaching the body to the second substrate is exposure to a plasma, such as an oxygen plasma.

FIG. 9 depicts another method for forming the nanostrips used to fabricate nanofluidic channels of the invention. The first steps are shown in FIG. 9A, in which e-beam lithography is used to pattern a photoresist deposited on a layer of chromium on the first substrate. The resulting structure has resist structures overlaying the chromium in the dimensions and positions desired for the nanostrips. The chromium is then etched using known conditions, producing a progressive removal of chromium between the resist structures, eventually exposing the substrate. Upon removal of the photoresist, nanostrips 7 remain on first substrate 5 in position for the formation of nanofluidic channels in the device.

Figure 10:
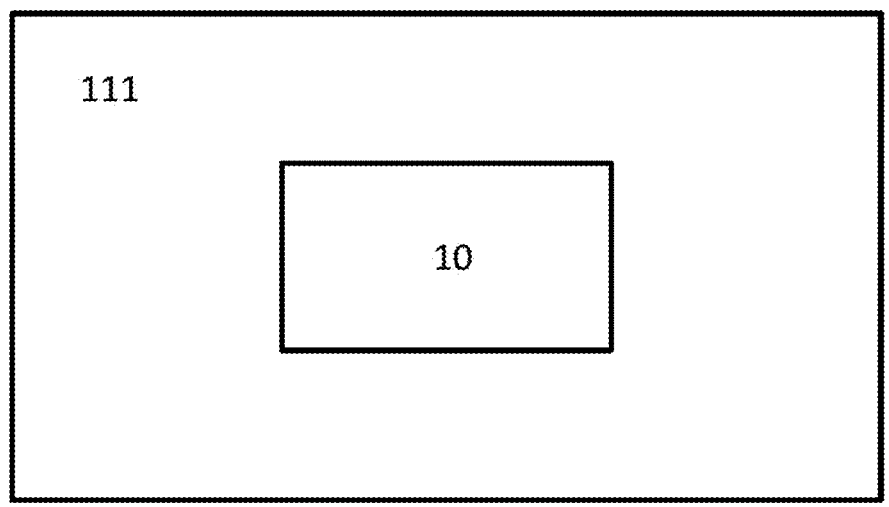
FIG. 10 shows an embodiment of a nanofluidic device of the invention that is part of an integrated circuit.

FIG. 10 shows another embodiment of device 10, in which the device is integrated into a circuit 111, such as part of an integrated circuit or CMOS device.

As used herein, "consisting essentially of" does not exclude materials or steps that do not materially affect the basic and novel characteristics of the claim. Any recitation herein of the term "comprising", particularly in a description of components of a composition, elements of a device, or steps of a method, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

The invention claimed is:

1. A method of isolating and culturing a microbial cell to obtain a monoculture of microbial cells, the method comprising the steps of:
   (a) exposing a fluid sample containing a mixture of microbial cells including said microbial cell to a device comprising a food chamber in fluid communication with an opening in the device, wherein the food chamber contains a culture medium containing a chemoattractant for said microbial cell and capable of supporting the growth and reproduction of said microbial cell, and wherein the opening allows only partial entry of said microbial cell;
   (b) allowing said microbial cell to migrate into the opening of the device;
   (c) maintaining the device under conditions suitable for allowing said microbial cell to divide while residing in the opening and produce progeny, whereby the progeny eventually enter the food chamber;
   (d) maintaining the device under conditions suitable for the progeny entering the food chamber to multiply in the food chamber, forming a monoculture of microbial cells.

2. A method of isolating and culturing a plurality of microbial cells to obtain a plurality of monocultures of microbial cells, the method comprising the steps of:
   (a) exposing a fluid sample containing a mixture of microbial cells to a device comprising a plurality of microfluidic food chambers, each fluidically coupled to a separate opening in the device, wherein the food chambers contain culture medium containing a chemoattractant for said microbial cells in the fluid sample and capable of supporting the growth and reproduction of said microbial cells in the fluid sample, and wherein the openings each allow only partial entry of one of said microbial cells in the fluid sample;

(b) allowing said microbial cells in the fluid sample to migrate into the openings of the device;

(c) maintaining the device under conditions suitable for allowing said microbial cells to divide while residing in the openings and produce progeny, whereby the progeny eventually enter the food chambers;

(d) maintaining the device under conditions suitable for the progeny entering the food chambers to multiply in the food chambers, forming a plurality of monocultures in said food chambers, each grown in a distinct food chamber of the plurality of chambers and derived from a distinct single microbial cell of the microbial cells in the fluid sample.

3. The method of claim 2, wherein the device comprises 100 or more food chambers, each fluidically coupled to a separate opening in the device.

4. The method of claim 2, whereby monocultures of two or more different species of microbes are obtained.

5. The method of claim 1, further comprising the step of:
(e) harvesting cells of the monoculture.

6. The method of claim 1, wherein a face of the food chamber comprises a membrane that permits entry of nutrients from an environment outside the food chamber but retains microbial cells within the food chamber, and wherein steps (c) and/or (d) are performed while supplying one or more additional nutrients through the membrane.

7. The method of claim 6, wherein the fluid sample was obtained from a natural environment, and wherein the one or more additional nutrients are supplied by a material obtained from said natural environment, said material placed in contact with the membrane attached to the food chamber.

8. The method of claim 7, wherein the microbial cells only grow and form a monoculture when the material obtained from the natural environment is placed in contact with the membrane.

9. The method of claim 2, wherein each of said plurality of food chambers contains a different culture medium, whereby microbial cells from the mixture are identified based on their ability to grow in one or more of the food chambers.

10. The method of claim 1, wherein any step of the method is monitored using light microscopy to observe the presence or identity of microbial cells.

11. The method of claim 1, wherein the method is performed autonomously.

12. The method of claim 1, wherein once a single microbial cell enters the opening, remaining microbial cells in the fluid sample are prevented from entering the food chamber.

13. The method of claim 1, wherein the fluid sample contains a mixture of different species of microbial cells, and wherein the monoculture of microbial cells produced in the food chamber represents a single species of microbial cells.

14. The method of claim 1, wherein the microbial cells are bacterial cells.

15. The method of claim 1, wherein at least during steps (a) through (c) the device is maintained in a natural environment.

16. The method of claim 15, wherein the device is submerged in soil, rock, or ice during at least steps (a) through (c).

17. The method of claim 1, wherein the opening has a diameter in the range from about 250 nm to about 1000 nm.

* * * * *